United States Patent [19]

Green, Jr. et al.

[11] Patent Number: 5,188,800
[45] Date of Patent: Feb. 23, 1993

[54] DENTAL IMPLANT SYSTEM

[75] Inventors: Ralph E. Green, Jr., Lexington, Mass.; Ronald H. Jones, South Burlington, Vt.; Leland J. Peters, Georgetown; Peter J. Withol, Natick, both of Mass.

[73] Assignee: Implant Innovations, Inc., West Palm Beach, Fla.

[21] Appl. No.: 775,292

[22] Filed: Oct. 10, 1991

Related U.S. Application Data

[62] Division of Ser. No. 205,606, Jun. 3, 1988, Pat. No. 5,071,351.

[51] Int. Cl.$^5$ ............................................. A61L 2/00
[52] U.S. Cl. ........................................ 422/23; 422/22
[58] Field of Search ................................ 422/22, 23

[56] References Cited

U.S. PATENT DOCUMENTS

| | | | |
|---|---|---|---|
| 2,857,670 | 10/1958 | Kiernan, Jr. | 433/175 |
| 3,579,831 | 5/1971 | Stevens et al. | 433/174 |
| 3,594,115 | 7/1971 | Wesley et al. | 422/22 |
| 3,732,621 | 5/1973 | Bostrom | 433/174 |
| 3,905,109 | 9/1975 | Cohen et al. | 433/174 |
| 3,948,601 | 4/1976 | Fraser et al. | 65/120 X |
| 4,065,817 | 1/1978 | Branemark et al. | 623/18 |
| 4,207,286 | 6/1980 | Gutboucher | 422/22 X |
| 4,253,833 | 3/1981 | Edelman | 433/173 |
| 4,262,631 | 4/1981 | Kubacki | 422/149 X |
| 4,313,911 | 2/1982 | Moran et al. | 422/159 |
| 4,330,891 | 5/1982 | Branemark et al. | 623/16 |
| 4,348,357 | 9/1982 | Bithell | 422/23 X |
| 4,391,773 | 7/1983 | Flanagan | 422/22 |
| 4,416,629 | 11/1983 | Mozsary et al. | 433/174 |
| 4,431,416 | 2/1984 | Niznick | 433/174 |
| 4,435,194 | 3/1984 | Picard et al. | 422/29 X |
| 4,439,152 | 3/1984 | Small | 433/173 |
| 4,447,209 | 5/1984 | Sutter | 433/173 |
| 4,457,221 | 7/1984 | Geren | 422/23 X |
| 4,464,336 | 8/1984 | Hiramoto | 422/24 |
| 4,466,796 | 8/1984 | Sandhaus | 433/173 |
| 4,468,200 | 8/1984 | Munch | 433/174 |
| 4,474,556 | 10/1984 | Ellis et al. | 433/173 |
| 4,479,783 | 10/1984 | Weissman | 433/221 |
| 4,486,178 | 12/1984 | Schulte | 433/173 |
| 4,524,079 | 6/1985 | Hofmann | 422/22 X |
| 4,531,915 | 7/1985 | Tatum, Jr. | 433/173 |
| 4,531,916 | 7/1985 | Scantlebury | 433/173 |
| 4,723,913 | 2/1988 | Bergman | 433/173 |
| 4,758,160 | 7/1988 | Ilsmail | 433/173 |
| 4,818,488 | 4/1989 | Jacob | 422/23 |
| 4,826,434 | 5/1989 | Krueger | 433/174 |

OTHER PUBLICATIONS

Predecki et al., *J. Biomed. Mater. Res.* (1972) 6:401–412.
Williams, *J. Medical Engineering Technology* (Sep. 1977) pp. 266–270.
Beder et al., *O.S., O.M. & O.P.* (1959) 12(7):787–799.
Branemark et al., *Osseointegrated Implants in the Treatment of the Endentulous Jaw*, Almquist & Wiksell International, Stockholm, Sweden, pp. 7–132.

*Primary Examiner*—Robert J. Warden
*Assistant Examiner*—Stephanie Blythe
*Attorney, Agent, or Firm*—Morrison & Foerster

[57] ABSTRACT

The dental implant system of the present invention has a decreased surface contact angle and includes a biocompatible titanium implant which has been treated by the plasma cleaning and sterilization process of the present invention.

An implant that has experienced plasma cleaning and sterilizing has improved retentive abilities over traditionally cleaned implants. The surface of the implant is now free of all organic debris, has increased wettability, contacts more bone-forming cells upon placement, and has stronger bonds between the metal surface and the bone-forming liquid cells. As a result, the implant becomes more intimately involved with the surrounding bone and tissue structure.

The implant is comprised of an inert, biocompatible titanium material that is designed of such dimensions and angulations to maximize contact the bone cells and subsequently attach a well-suited mechanical prosthetic system to it.

18 Claims, 2 Drawing Sheets

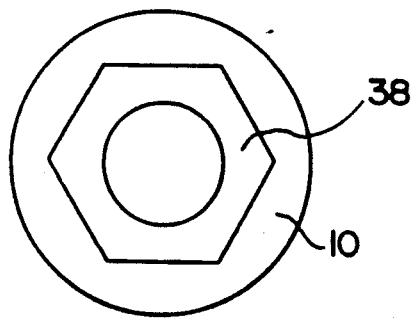
FIG. IA
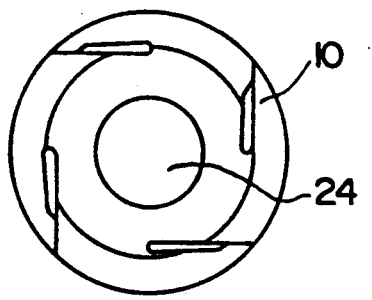
FIG. IB
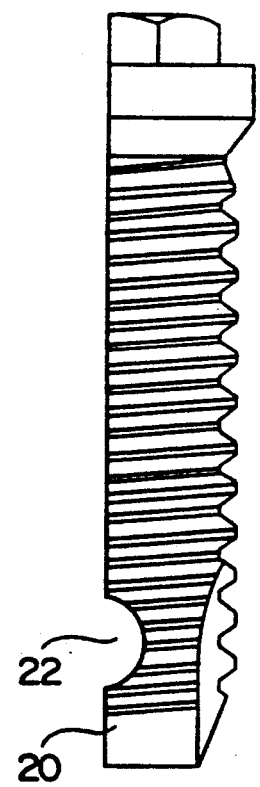
FIG. 2
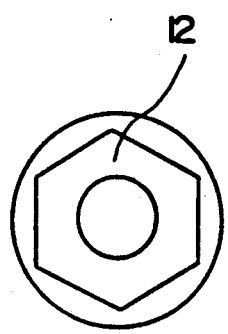
FIG. IC
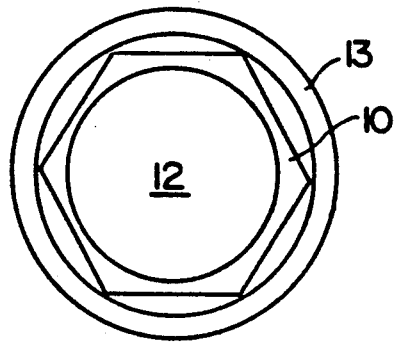
FIG. ID

DENTAL IMPLANT SYSTEM

This application is a division of application Ser. No. 07/205,606 filed, Jun. 3, 1988 (now U.S. Pat. No. 5,071,351).

FIELD OF THE INVENTION

The present invention relates to a novel dental implant and to a novel method of preparing such materials for implantation. The implant of the present invention serves as a permanent replacement for natural teeth.

BACKGROUND OF THE INVENTION

The successful replacement of lost teeth by implant-fastened prosthesis would especially improve the quality of life for thousands of middle-aged and elderly edentulous patients who suffer from advanced residual ridge reduction. These individuals cannot cope with conventional prostheses and often confront the dental profession with problems that cannot readily be solved.

The edentulous and partially edentulous jaw areas are typical examples of tissue defects that cause different degrees of functional disturbances. A well-fitting prosthesis appears to be an acceptable alternative to natural teeth as long as the anatomy of the residual hard and soft tissues provides good retention for the prosthesis. Progressive loss of alveolar bone and the spreading of dental caries tends to undermine the relative stability of the prosthesis, and can create severe problems of both a functional and psychosocial nature.

Numerous dental implant systems have been designed for the prosthetic replacement of natural teeth. These systems have made use of screws, nails, blades, shanks or pins which serve as the anchor of the prosthetic attachment, and a superstructure which replaces the natural tooth. Several of the implants of this type resulted in the formation of fibrotic tissue around the implant, insufficient gingival sealing, chronic infection, and bone loss leading to the eventual failure of the implant. Improvements of the early implant systems have been made, but a totally effective implant has heretofore been unavailable.

Patent and publications describing previous implant systems include the following; Schulte, U.S. Pat. No. 4,486,178; Scantlebury et al., U.S. Pat. No. 4,531,916; Tatum, Jr., U.S. Pat. No. 4,531,915; Sandhaus, U.S. Pat. No. 4,466,796; Small, U.S. Pat. No. 4.439,152; Niznick, U.S. Pat. No. 4,431,416; Mozsary et al., U.S. Pat. No. 4,416,629; Branemark et al., U.S. Pat. No. 4,330,891; Branemark et al., U.S. Pat. No. 4,065,817; Cohen et al., U.S. Pat. No. 3,905,109; Stevens et al., U.S. Pat. No. 3,597,831; Predecki et al., J. Biomed. Mater. Res., 6: 401 (1972); Williams, J. Med. Eng. Tech., 266 (1977); Beder et al., O.S.,O.M. & O.P., 787 (1959); Branemark et al., "Osseointegrated Implants in the Treatment of the Edentulous Jawn", Scan. J. Plas. Recon. Suro., Vol. 11, Suppl. 16, (1977).

Different procedures have been advocated to implant dental prosthesis in the soft or hard tissues of the edentulous and partial edentulous jaw. However, long-term clinical follow-ups indicate that such procedures do not provide predictable long-term function. Attempts at implanting an implant by means of a regenerated fibrous tissue layer forming a simulated periodontal ligament have also been unsuccessful.

It has been stated in the bone reconstruction literature that direct implantation into living bone of load-bearing implants does not work over the long run. It has also been stated that the design of the implant surface structure is very important for success. The novel design of the present invention refutes the first of these statements and confirms the second.

During the manufacture of metal dental implants, cutting oils are used to enhance cutting tool action and to serve as a coolant for the cutting tool itself. The traditional methods of "degreasing", or removing these oils after manufacture, include rinsing in a sequence of different solvents which often leave residues of hydrocarbons on the surface of the implant. In addition a "deburring" process takes place to remove burrs and rough edges from the implant. This process may utilize either mechanical or chemical methods or both.

The implant is then rinsed, with an inorganic or organic solvent, depending on which deburring process is used. The rinsing process is employed to remove abrasive particulates, and to prevent further introduction or new contamination of the implant surface. Typically the implant surface is still contaminated with, for example: a mono-layer of hydrocarbons from the cutting oil; residual particulates from the abrasive cleaning processes; metal dust; airborn dust; residual salts; and inorganic materials.

The ultimate cleanliness of the implant is determined by the subsequent manufacturing steps. These next steps usually take place in a "clean room" facility. These may include subsequent ultrasonic rinsing with organic solvents such as freon, trichlorethylene, or various alcohols, or inorganic solvents, such as deionized or distilled water. After the rinsing process, a mono-layer of contaminants may still remain on the surface of the implant. The implant is usually packaged with these contaminants still on the surface.

Careful preparation of the implant surface by traditional cleaning before use generally reduces the quantity of contaminants. Standard sterilizing of these implants does render them free of live bacteria but tends to increase surface contamination by allowing salts to accumulate as a product of steam autoclaving. Another drawback to conventional autoclaving is the presence of deceased microorganisms on the surface of the sterilized article. The presence of such materials may interfere with the integration of the implants into the surrounding bone/tissue.

Patents describing sterilization and/or cleaning methods include; Hofmann, U.S. Pat. No. 4,524,079; Hiramoto, U.S. Pat. No. 4,464,336; Geren, U.S. Pat. No. 4,457,221; Flanagan, U.S. Pat. No. 4,391,773; Gut Boucher, U.S. Pat. No. 4,207,286; Fraser et al., U.S. Pat. No. 3,948,601 and Wesley et al., U.S. Pat. No. 3,594,115.

The method of the present invention was developed to overcome the difficulties associated with the traditional cleaning methods used for implants. The method of the present invention utilizes a plasma cleaning device to ensure the cleanliness and sterility of the entire implant system, thus assuring that the design of the present invention will have increased retentive properties as well as a good and predictable long-term prognosis.

SUMMARY OF THE INVENTION

The present invention is preferably directed to a novel and useful dental implant system and to a method of cleaning this implant system and other implant systems, such that the retentive properties thereof are enhanced.

As used herein, the term "implant" refers to any anchor-, fastener-, fixture-, root-, member or means, designed to be embedded or implanted at least partially within mammalian, preferably human, bone tissue. Implants may be prepared from virtually any suitable biocompatible material, e.g., titanium, vitalium, stainless steel, titanium alloys, tricalcium phosphate, hydroxy apatite, ceramics, and the like.

The first aspect of the present invention represents a break from the traditional cleaning and rinsing processes normally employed for the preparation of dental implants, wherein the novel dental implants of the present invention are processed in a plasma cleaning device.

Following plasma cleaning, the implants of the present invention are cleaner, and have fewer contaminants on the surface, than those implants prepared using conventional cleaning and sterilization techniques. The advantages of the cleaning process of the present invention include:

(a) residues or mono-layers of organic material from cutting oils are removed; and (b) residues from the cleaning solvents are removed.

Moreover, due to the nature of the plasma cleaning process, the surface energy and surface area is increased on the implant, and the surface contact angle (as determined by the method of O'Brien et al., J. Prosthet. Dent., 15: 305 (1965)), is reduced from about 30° to approximately 20°, preferably to less than about 10°, and most preferably to less than about 5°. The "contact angle" referred to herein is the angle formed between a drop of water on the solid implant surface and the surface itself. This reduction in surface contact angle leads ultimately to strengthened bonds between the metal surface and the bone forming cells.

In some cases, particulate contamination from deburring is not removed by plasma cleaning alone, and thus it is sometimes necessary to soak and rinse the implant in either an organic or inorganic solvent, preferably in an ultrasonic device, prior to plasma cleaning.

Thus, the most preferred cleaning process of the present invention, for use with biocompatible implant systems, involves two cleaning steps:

(1) particulate removal by ultrasonic cleaning with an appropriate organic and/or inorganic solvent; and (2) plasma cleaning for ultimate purification of the implant system surface.

During the plasma cleaning of the preferred titanium implant, the surface of the implant is thoroughly cleaned of all hydrocarbon monolayers. The preferred plasma cleaning process utilizes:

(a) an inert gas or a mixture of gases;

(b) a vacuum from about 100 to 5000 microns;

(c) a time period of from about 1 to 10 minutes; and (d) an RF power source (e.g., an oscillator or crystal) of from about 50 watts to about 1 kilowatt; to effectively remove the surface contaminants while not affecting the physical or chemical properties of the titanium surface.

Thus, the cleaning method of the present invention provides an improved implant system which leads to ideal retention of the implant.

The second aspect of the present invention is directed to a unique implant system which includes the following component parts:

1. a biocompatible titanium screw implant which has been processed, preferably in a plasma cleaning device, to decrease the surface contact angle from about 30° to less than about 20°, preferably less than about 10°, most preferably less than about 5°, while not affecting the physical or chemical properties of the surface of the implant;

2. a biocompatible, plasma cleaned titanium screw implant which has been processed, preferably in a plasma cleaning device, and has been cleaned and sterilized at the surface, from organic contamination of the implant to provide a biologically clean and sterile surface;

3. a biocompatible, plasma cleaned titanium screw implant which is versatile in design to mechanically support (a) individual teeth in the form of a single crown, and (b) a group of teeth in the form of a fixed bridge, fixed denture, and fixed over-denture;

4. a biocompatible, plasma cleaned titanium screw implant of such geometrical shape and dimensions that a well-suited prosthetic system can be attached to it;

5. a biocompatible, plasma cleaned titanium screw implant whose surface heals in a more direct and intimate relationship to the architecture of the bone;

6. a biocompatible, plasma cleaned titanium screw implant that has up to four axially extending notches that comprise 15% to 95% of the total length of the implant;

7. a screw implant that has been processed in a plasma cleaning device whereby the energy content of molecules at the interface has been changed such that the surface energies and surface areas have been increased compared to screw implants that have not been processed in plasma cleaning devices;

8. a screw implant that has been processed in a plasma cleaning device having stronger bonds between the titanium implant surface and the bone forming cells;

9. a biocompatible, plasma cleaned titanium screw implant which it is believed will have a higher success rate as compared to the prior art implants, e.g., blades, alternative type screws, baskets, and ceramic implants;

10. a biocompatible pillar part which has been processed, preferably in a plasma cleaning device, to decrease the surface contact angle of about 30° to approximately 20°, preferably less than about 10°, most preferably less than about 5°, while not affecting the physical or chemical properties of the surface; and 11. a biocompatible titanium pillar part which has been processed, preferably in a plasma cleaning device, and has been cleaned and sterilized at the surface from organic contamination of the implant to provide a biologically clean and sterile surface.

In use, the present implant is implanted into the jaw bone (alveolar) in a drilled opening. The system has a lower portion which extends into the jaw bone and an upper portion which is accessible from the outer surface of the jaw bone. The wall of the implant further defines a cylindrical hollow core which extends from the upper end about ⅔ of the way to the lower end thereof. The implant includes a threaded surface and self tapping means, which allow for stable insertion into the opening within the jaw bone. Means for securing the implant in place within the jaw bone, such as horizontal and vertical passages, are incorporated into the lower portion of the implant.

The hollow in the surface par of the present implant system defines a cylindrical space for the placement of a pillar post, which provides the means of support for the remainder of the prosthetic implant system. The lower portion of the pillar post is a solid member, threaded in a manner which is acceptable to the threads contained within the hollow of the implant. The wall of the upper portion of the pillar post defines a threaded cylindrical hollow. A hollow pillar cylinder surrounds that portion of the pillar post above the implant and supports a crown which is attached thereto by an attachment means such as a prosthetic screw.

While the present invention will be described in detail with respect to the preferred embodiments thereof, namely dental implants of the screw type, other medical implants such as blades, baskets, and the like, whether made of titanium, alloys thereof, ceramics or the like, may be treated in accordance with the teachings of the present invention, and it is believed that similar beneficial aspects in performance will occur.

BRIEF DESCRIPTION OF THE DRAWINGS

A detailed description of the preferred embodiment of the present invention will be made with reference to the accompanying drawings wherein like numerals designate corresponding parts in the several figures.

FIG. 1A is a view along section line 1A—1A of the implant of the present invention showing the upper surface of the biocompatible screw implant;

FIG. 1B is a view along section line 1B—1B of the implant of the present invention showing the lower surface of the biocompatible screw implant;

FIG. 1C is a view along section line 1C—1C of the implant of the present invention showing the upper portion of the pillar surface.

FIG. 1D is a view along section line 1D—1D of the implant of the present invention showing the lower portion of the pillar surface.

FIG. 2 is a longitudinal view of the implant of the present invention.

DETAILED DESCRIPTION OF THE PREFERRED EMBODIMENT

Figure 1:
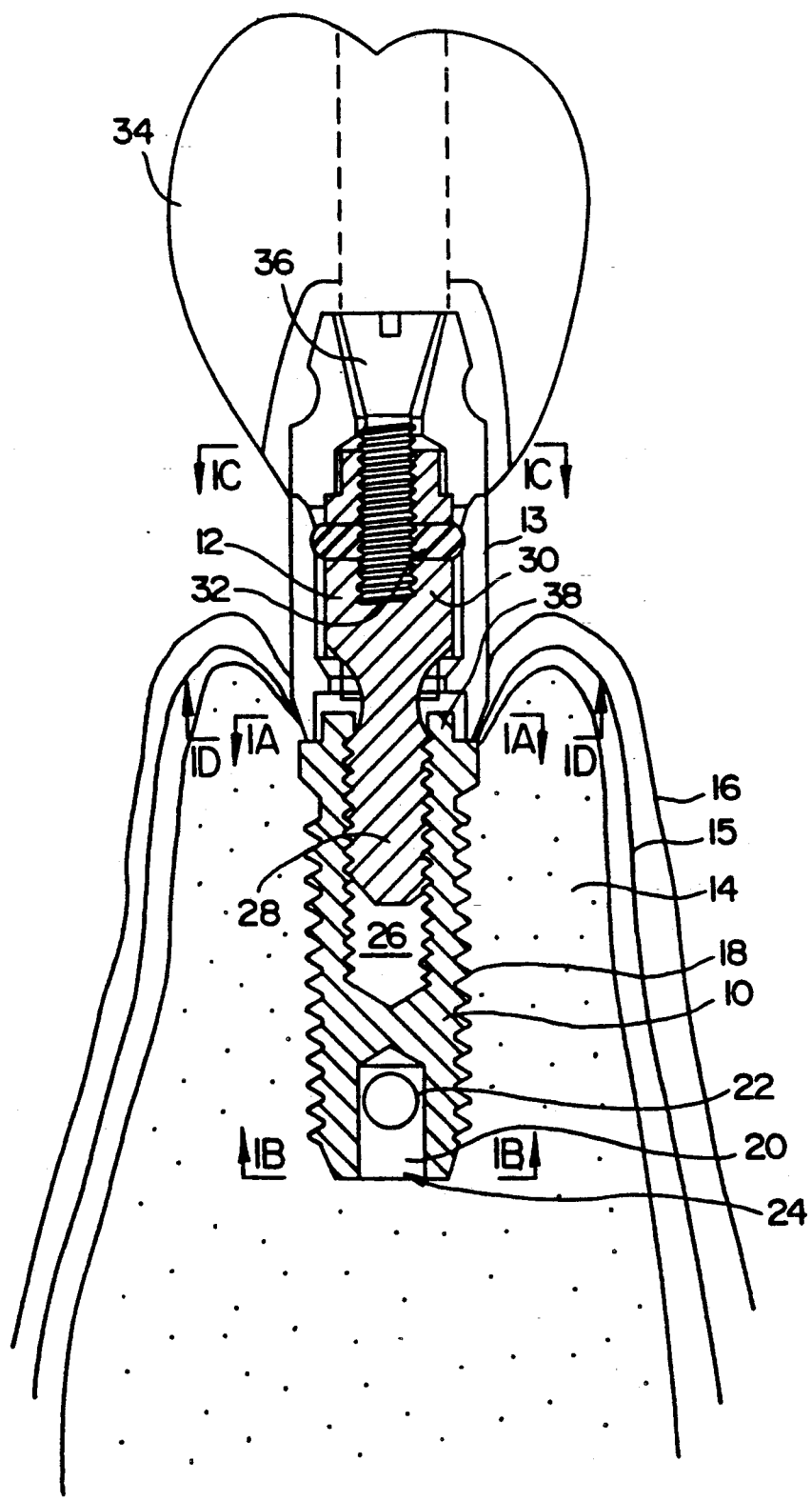
FIG. 1 is a sectional view of an embodiment of the present invention showing the implant situated in a portion of the jaw and gum.

A preferred embodiment of the dental implant system of the present invention is illustrated in FIGS. 1, 1A-1D, and 2.

The implant 10 and companion pillar parts 12 (the solid pillar post) and 13 (the hollow pillar cylinder) are preferably prepared from biocompatible titanium materials, such as commercially pure (CP) grades of titanium metal or alloys thereof.

The entire structure may be readily and accurately machined so as to have the illustrated construction. As set forth by Branemark ("Osseointegrated Implants," p. 27, supra), irregularities in the surface of the titanium implant are an artifact of the manufacturing process. Such irregularities, e.g., pitting, the "moon-like" rutile surface, etc., are known to serve as attachment sites between the tissue and the implant.

The implant 10 may be formed in various lengths and widths, as may be the companion pillar parts 12 and 13, depending upon the specific dimensions of the jawbone into which it will be implanted.

The jaw bone (alveolar) 14 is prepared with drills of increasing dimensions, utilizing a gentle surgical technique, to pierce the gingiva 16 and the outer cortical bone 15, followed by a titanium tap device to create a corresponding shaped recess for insertion of the implant.

The implant 10 is retained in the recess of the jaw bone 14 by means of a tight fit therein. The threads 18 at the lower region of implant 10 are preferably of the self-tapping type in order to enhance the stability of the implant.

The lower portion of the implant 10 may be provided with up to four axially extending notches 20 which extend over from about 15% to 95% of the total length of the implant 10 so as to provide the lower region thereof with one or more cavities into which the tissue of the bone can grow and become secure in an intimate connection between the implant and the bone structure. In addition, the lower end of the implant 10 may be provided with one or more horizontal openings 22 and/or vertical openings 24 into which the tissue of the bone can grow and form a secure connection with the implant.

The extent to which the implant is surgically placed is precisely controlled so that at the region where the implant is to be located there is no interference with any body cavities, sharp curvatures, or small thickness.

Several implants may be arranged so that they will be situated approximately in planes parallel to planes tangent to the exterior surfaces of the jawbone structure, with both lower and upper surfaces imbedded into the cortical plates. Such placement assures an extremely secure mounting.

As described above, the implant of the invention may be provided in different forms, e.g., various lengths, widths, etc., so that the dentist will have available absolutely clean and sterile implants of different sizes and lengths, one of which will be the most suitable for the particular conditions which are encountered in any given patient. Typical dimensions of the preferred implants of the present invention includes widths of 3.75 mm and 4.0 mm and lengths ranging from 4 to 20 mm.

The upper portion of the implant 10 defines a cylindrical hollow section 26 which is threaded to accept a lower portion 28 of pillar post 12, which provides the means of support for the remainder of the prosthetic implant system. The lower portion 28 of pillar post 12 is a solid member, threaded in a manner which is acceptable to the threads contained within the hollow 26 section of the implant 10.

The wall 30 of the upper portion of pillar post 12 defines a threaded cylindrical hollow 32. A hollow pillar cylinder 13 surrounds that portion of the pillar post 30 which rests above the implant 10 and supports a crown 34 which is attached thereto through the threaded portion of the pillar post 32 by means of an attachment means such as a prosthetic screw 36.

FIG. 1 illustrates the implant 10 positioned in the jaw bone 14. As illustrated, the implant 10 is designed to support both of the companion pillar parts 12 and 13. The companion pillar parts 12 and 13 may be connected to other attachments as the dentist may desire.

The implant 10 is preferably of uniform shape and has peripheral threads of a specific design which maximize the axial load carrying capacity and the contact area available between the implant and bone. The surface contact angle of the implant prior to plasma cleaning treatment is generally about 30° and after plasma cleaning treatment is reduced to approximately 20°, preferably less than about 10°, and most preferably less than about 5°.

While not wishing to be bound by theory, it is believed that the plasma cleaning processing of the implant of the present invention affects the contact angle between the solid implant surface and the medium within the implant recess. The contact angle, i.e., the angle of formed between a tangent of a liquid droplet and a solid surface upon which the droplet sits, can be measured experimentally or may be inferred by the rate of spreading of a liquid in contact with the solid. See O'Brien et al., supra.

When the contact angle is zero (or theoretically less), the attraction of a liquid for the solid is exactly equal to (or greater than) the attraction of the liquid to itself, and complete wetting of the solid readily occurs at equilibrium. Contact angles of from about 30° and up are associated with low solid-liquid adhesion properties. That is, wetting of a surface having a high contact angle occurs slowly and often incompletely. A theoretical maximum contact angle of 180°, which would indicate the complete absence of solid-liquid adhesion, is not known to exist.

After treatment of the implant of the present invention in a plasma cleaning device, the surface of the implant is ultra clean. When placed in contact with a droplet of blood, the blood races up the threads of the screw by capillary action. In comparison, implants treated by conventional cleaning methods (heat sterilization, organic solvent washings, etc.) when placed in contact with a droplet of blood, show sluggish attraction of the surface of the implant to the liquid medium.

As described in connection with the illustration of the preferred embodiment, the lower end of the implant is most preferably hollow in two dimensions; vertically, through an opening in the bottom surface, and horizontally through an opening which connects the outer diameters of the implant. This dual opening allows the ingrowth of bone tissue and creates a locking shape which provides the means for preventing extraction of the implant due to torquing forces.

The outer surface of the most preferred implant has up to four axially extending notches whose extensions comprise 15% to 95% of the total length of the implant. The notches enhance the self-threading action of the screw means. In addition, the notches form a cavity into which the bone tissue can grow and provide an absolutely secure and intimate connection of the implant in the bone structure.

As illustrated in FIGS. 1D and 2, the upper end of the most preferred implant contains a hexagonal mount 38 and internal threads which serve as the means of attachment for the companion pillar parts. In the preferred embodiments, the companion pillar parts are also composed of biocompatible titanium materials which have been plasma cleaned to improve the adhesion between the surface of the pillar and the hard and soft tissues of the oral cavity. The contact angle of the pillar parts prior to plasma cleaning treatment is generally about 30° and after plasma cleaning treatment is approximately 20, preferably less than about 10°, most preferably less than about 5°.

The preferred companion pillar parts are connected to the implant by the attachment means after a healing period, which may range from about three to six months. The companion pillar parts extended upward from the top surface of the screw implant through the soft tissues of the gum and exit into the oral cavity one to two millimeters above the outer surface of the soft tissues.

While the design of the present implant offers advantages over prior art implants, the preferred cleaning method of the present invention may be used to improve the performance of any medical or dental implant.

The unique cleaning method of the present invention includes a cleaning and sterilizing process which is conducted prior to the surgical placement of the implant.

The cleaning process of the present invention involves utilizing a plasma cleaning device at a power rating between about 50 watts to 1 kilowatts, preferably with an inert gas or inert gas mixture. Other gases may be used, including air, but the time required to effect complete cleaning and sterilization may need to be increased.

The plasma cleaning device preferably includes means for providing a vacuum between about 100 to 5000 microns, either by a single or double stage mechanical roughing pump, or the like. If desired, an ultra low vacuum may be provided, e.g., by a diffusion pump. Preferably, there is a vacuum gauge and means, such as a tube to monitor the vacuum level, and a high efficiency filter to filter the air of any bacteria when the vacuum chamber is vented. Likewise, a sorbant or high efficiency, high surface area filter is preferably incorporated into the system to trap any vacuum pump vapors which might "back stream" or migrate from the vacuum pump back into the purification chamber. There may also be included an exhaust filter to trap pump vapors coming out of the vacuum pump and going into the air in the general vicinity of the plasma cleaning device.

It has been discovered that, when using the preferred plasma cleaning purification method and apparatus of the present invention, that a time frame of from about one minute to ten minutes is adequate to sufficiently clean the surface of the implant of all common organic residues which result from the manufacturing process or the surgery preparation procedure. This time period is also sufficient to sterilize the surface of the implant.

While not wishing to be bound by theory, it is believed that the use of the preferred plasma cleaning device of the present invention changes the energy content of the molecules at the interface between the titanium implant and the bone forming cells. The surface energies and surface areas are increased, creating stronger bonds between the titanium implant surface and the bone forming cells.

In the preferred embodiments, a commercially available plasma cleaning unit, such as the 100 watt mode RF glow discharge device from Harrick Scientific is modified as described herein and used.

The preferred plasma cleaning unit is utilized with ultra high purity argon gas, and a single or double stage mechanical roughing pump capable of reaching 20 microns of vacuum or less.

A vacuum gauge and tube monitor the vacuum levels. A high efficiency filter is used to filter the air of bacteria when the vacuum chamber is vented. A sorbant or high efficiency, high surface area filter is used to trap any vacuum pump vapors which might "back stream" or migrate from the vacuum pump back to the implant chamber.

An exhaust filter is used to trap pump vapors coming out of the vacuum pump and going into the air in the general vicinity of the plasma cleaning device. A sample or implant holder with both pins and holes and made of pure titanium is used to hold the implants in the area of maximum glow.

The implant is placed in the sample chamber, which is pumped to a medium vacuum. An inert gas (preferably argon) is then admitted to the chamber at a pressure of about 1 torr. The vacuum pump is again activated to draw down the vacuum to operating pressures. The RF power supply is turned on at maximum power for a period of less than five minutes. At the end of processing filtered air is admitted to the chamber and the cleaned and sterile implants are removed. While not wishing to be bound by theory, it is currently believed that the implants are bombarded by low energy ions and electrons during the plasma cleaning process and that the impurities are desorbed from the surface due to the ion and electron bombardment.

In addition to the above-described preferred plasma cleaning embodiment, the following additions and/or modifications may be incorporated herein:

1. alternating high and low vacuums causing a pulsing of the inert argon gas may increase the ability of the ions to enter into blind holes and crevices thus creating more rapid cleaning and sterilization.

2. utilizing the inert gas krypton might give more efficient cleaning and sterilization due to the heavier molecular weight; utilizing a mixture of argon/krypton may also give more efficient cleaning and sterilizing and be less expensive to use than pure krypton.

3. Other gases may similarly be employed, e.g., organic gases, e.g., butane and the like. Even air, if sufficient time for sterilization and cleanliness are provided, will work.

4. utilizing an electrode plasma cleaning device with oxygen may produce more efficient cleaning and sterilization than an RF plasma cleaning device; the implants could then be placed on individual cathodes which would act as part of the packaging device.

5. utilizing an intense high frequency discharge could also be generated with use of a tesla coil attached to a cathode holder similar to #3.

6. utilizing a plasma cleaner may give more efficient cleaning and sterilization; a rotating drum insert of titanium mesh could be used to tumble the implants during processing, affecting all surfaces.

7. utilizing a higher powered plasma cleaning device may be utilized to etch pits in the surface of the implants to produce a surface structure more conductive to growth and attachment of bone cells to the implant surface.

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. A method of cleaning and sterilizing a biocompatible implant, comprising the steps of:
   placing the implant in a plasma cleaning device;
   securing the implant to the device with a holding means;
   subjecting the implant to a flow of substantially pure gas; and
   continually removing gas from the plasma cleaning device so as to maintain a vacuum in the plasma cleaning device in the range of about 20 to about 5,000 microns of vacuum and continuing the flow and the vacuum for a period of time sufficient to clean and sterilize the implant and until a surface of the implant develops a surface contact angle of about 20 degrees or less.

2. The method as claimed in claim 1, wherein the surface contact angle is about 10 degrees or less.

3. The method as claimed in claim 2, wherein the surface contact angle is approximately 5 degrees or less.

4. The method as claimed in claim 1, wherein the gas is an inert gas.

5. The method as claimed in claim 4, wherein the inert gas is a gas selected from the group consisting of krypton, argon, and mixtures thereof.

6. The method as claimed in claim 1, wherein the gas is oxygen.

7. The method as claimed in claim 1, further comprising:
   monitoring the vacuum in the plasma cleaning device by means of a pressure gauge.

8. The method as claimed in claim 1, wherein the gas is subjected to a filter prior to entering the plasma cleaning device.

9. The method as claimed in claim 1, wherein gas is removed from the plasma cleaning device and the removed gas is filtered through a gas filter.

10. The method as claimed in claim 1, wherein the plasma cleaning device is powered by 50 watts or more of power over a period of time of from about 1 to about 10 minutes.

11. The method as claimed in claim 1, wherein the vacuum is maintained by a single stage roughing pump.

12. The method as claimed in claim 1, wherein the vacuum is maintained by a double stage roughing pump.

13. The method as claimed in claim 1, further comprising:
   cleaning any particulate materials from the dental implant by subjecting the dental implant to ultrasonic energy while the dental implant is held in a solvent, the cleaning being carried out prior to placing the dental implant system in the plasma cleaning device.

14. The method as claimed in claim 13, wherein the solvent is an organic solvent.

15. The method as claimed in claim 13, wherein the solvent is an inorganic solvent.

16. The method as claimed in claim 1, wherein the dental implant is subjected to pulsating flows of inert gas by allowing the vacuum in the device to fluctuate.

17. The method as claimed in claim 1, further comprising:
   subjecting the dental implant to electrolysis by placing the dental implant between an anode and a cathode and causing a current differential to exist between the anode an the cathode.

18. The method as claimed in claim 1, further comprising:
   subjecting the dental implant to an intense high frequency discharge generated by a Tesla coil attached to a cathode.

* * * * *